United States Patent [19]
Valtchev

[11] Patent Number: 5,100,382
[45] Date of Patent: Mar. 31, 1992

[54] SINGLE CHANNEL BALLOON UTERINE INJECTOR

[76] Inventor: Konstantin L. Valtchev, 43 Cosmic Drive, Don Mills, Toronto, Ontario, Canada, M3B 3G1

[21] Appl. No.: 261,078

[22] Filed: Oct. 24, 1988

[51] Int. Cl.⁵ .......................................... A61M 29/00
[52] U.S. Cl. ................................................. 604/96
[58] Field of Search ............................. 604/96–103; 600/18; 128/344

[56] References Cited

U.S. PATENT DOCUMENTS

| | | | |
|---|---|---|---|
| 3,504,662 | 4/1970 | Jones | 128/344 |
| 3,692,018 | 9/1972 | Goetz et al. | 600/18 |
| 3,916,906 | 11/1975 | Gerry | 128/344 |
| 4,022,208 | 5/1977 | Valtchev . | |
| 4,029,104 | 6/1977 | Kerber . | |
| 4,290,428 | 9/1981 | Durand et al. | 604/96 |
| 4,301,803 | 11/1981 | Handa et al. | 604/103 |
| 4,573,476 | 3/1986 | Ruiz . | |
| 4,575,371 | 3/1986 | Nordqvist et al. . | |
| 4,652,258 | 3/1987 | Drach . | |
| 4,655,745 | 4/1987 | Corbett . | |
| 4,811,737 | 3/1989 | Rydell | 128/344 |

FOREIGN PATENT DOCUMENTS 3634569   4/1988   Fed. Rep. of Germany ........ 604/49

OTHER PUBLICATIONS

Brochure entitled The Valtchev Uterine Mobilizer, undated, Conkin Surgical Instruments Ltd.

*Primary Examiner*—C. Fred Rosenbaum
*Attorney, Agent, or Firm*—Henderson & Sturm

[57] ABSTRACT

An apparatus for injection of dye or contrast medium into a uterine cavity. An elongated member having a first and a second end and an intermediate portion has a liquid impervious expandable tube disposed around it and is sealed on each end thereof to the exterior thereof. A first fluid passageway extends from one end of the elongated member to a barrier and another fluid passageway extends from the other end of the elongated member to the barrier. A first opening in the elongated member allows fluid communication between the first passageway and the inside of the balloon tube and a second opening in the elongated member provides fluid communication between the second fluid passageway and the inside of the balloon tube. The second opening is substantially smaller in cross-sectional area than the first opening whereby fluid pressure applied to the first passageway will remain substantially higher than the pressure in the second fluid communication passageway, whereby fluid pressure within the tube will cause it to expand to seal against the inner wall of the uterine cavity, while at the same time fluid will flow sequentially from the first fluid communication passageway, through the first opening, through the expanded balloon tube, through the second opening, through the second communication passageway and out through a discharge opening structure on one end of the second fluid communication passageway.

4 Claims, 3 Drawing Sheets

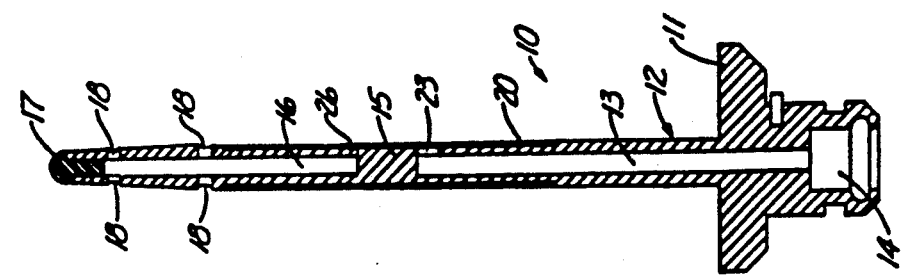
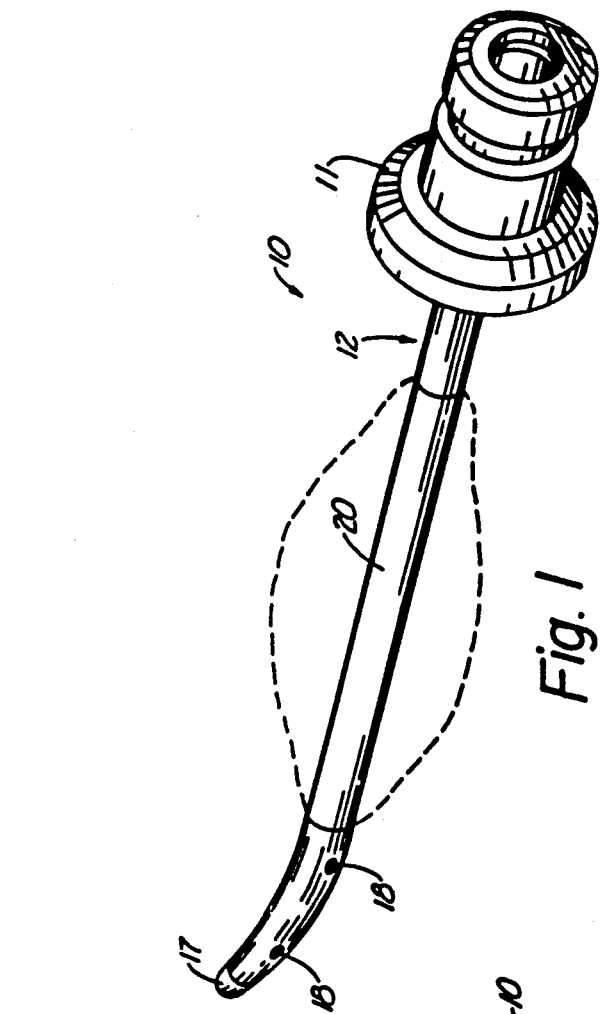
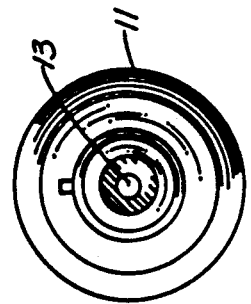
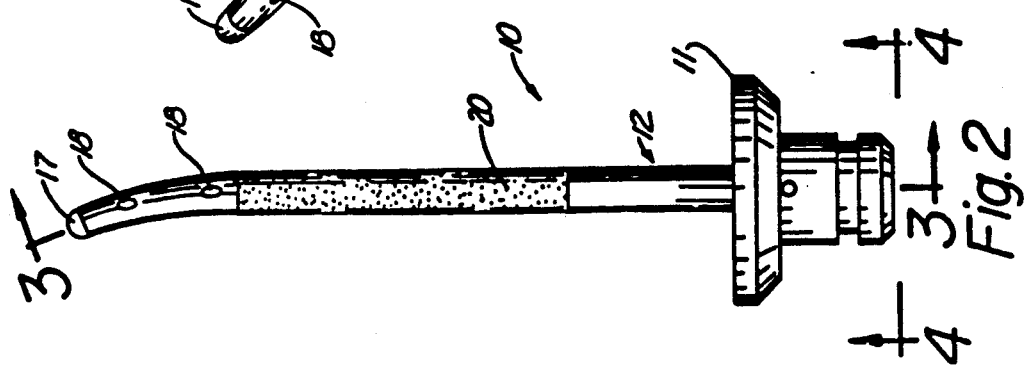

SINGLE CHANNEL BALLOON UTERINE INJECTOR

TECHNICAL FIELD

The present invention relates generally to a uterine injector, and more particularly to a single channel balloon-type uterine injector.

BACKGROUND ART

There are different instruments available for injection of dye or x-ray contrast medium into the uterine cavity. In order to seal the vaginal opening of the uterus (external os) some of the cannulas have an acorn which is pushed against the external os and insures leak proof application. Sometimes, however, the sealing of the external os fails.

In an attempt to overcome this problem, another instrument was developed. This instrument consists of two channels, one for injection of dye or x-ray contrast medium, and the second for inflating a balloon inside the uterine cavity. This structure seals the external os and prevents leaking. The disadvantages of the cannula with balloon instrument is its cumbersome construction and its high cost.

DISCLOSURE OF THE INVENTION

The present invention relates to an apparatus for injection of dye or contrast medium into a uterine cavity. An elongated member having a first and a second end and an intermediate portion has a liquid impervious expandable tube disposed around it and is sealed on each end thereof to the exterior thereof. A first fluid passageway extends from one end of the elongated member to a barrier and another fluid passageway extends from the other end of the elongated member to the barrier. A first opening in the elongated member allows fluid communication between the first passageway and the inside of the balloon tube and a second opening in the elongated member provides fluid communication between the second fluid passageway and the inside of the balloon tube.

The second opening is substantially smaller in cross-sectional area than the first opening whereby fluid pressure applied to the first passageway will remain substantially higher than the pressure in the second fluid communication passageway, whereby fluid pressure within the tube will cause it to expand to seal against the inner wall of the uterine cavity, while at the same time fluid will flow sequentially from the first fluid communicaiton passageway, through the first opening, through the expanded tube, through the second opening, through the second communication passageay and out through a discharge opening structure on one end of the second fluid communication passageway.

An object of the present invention is to provide an improved uterine injector.

A further object of the present invention is to provide an improved uterine injector which is simpler to use than the prior art uterine injectors.

A further object of the present invention is to provide a uterine injector which is dependable to use and which is economical to produce.

Other objects, advantages, and novel features of the present invention will become apparent from the following detailed description of the invention when considered in conjunction with the accompanying drawings.

BRIEF DESCRIPTION OF THE DRAWINGS

FIG. 1 is a perspective view of a single channel balloon uterine injector apparatus constructed in accordance with the present invention and showing in dashed lines how the balloon-like tube can be expanded;

FIG. 2 is a top view of the uterine injector of FIG. 1;

FIG. 3 is a cross sectional view taken along line 3—3 of FIG. 2;

FIG. 4 is a view taken along line 4—4 of FIG. 2;

BEST MODE FOR CARRYING OUT THE INVENTION

Figures 5, 6:
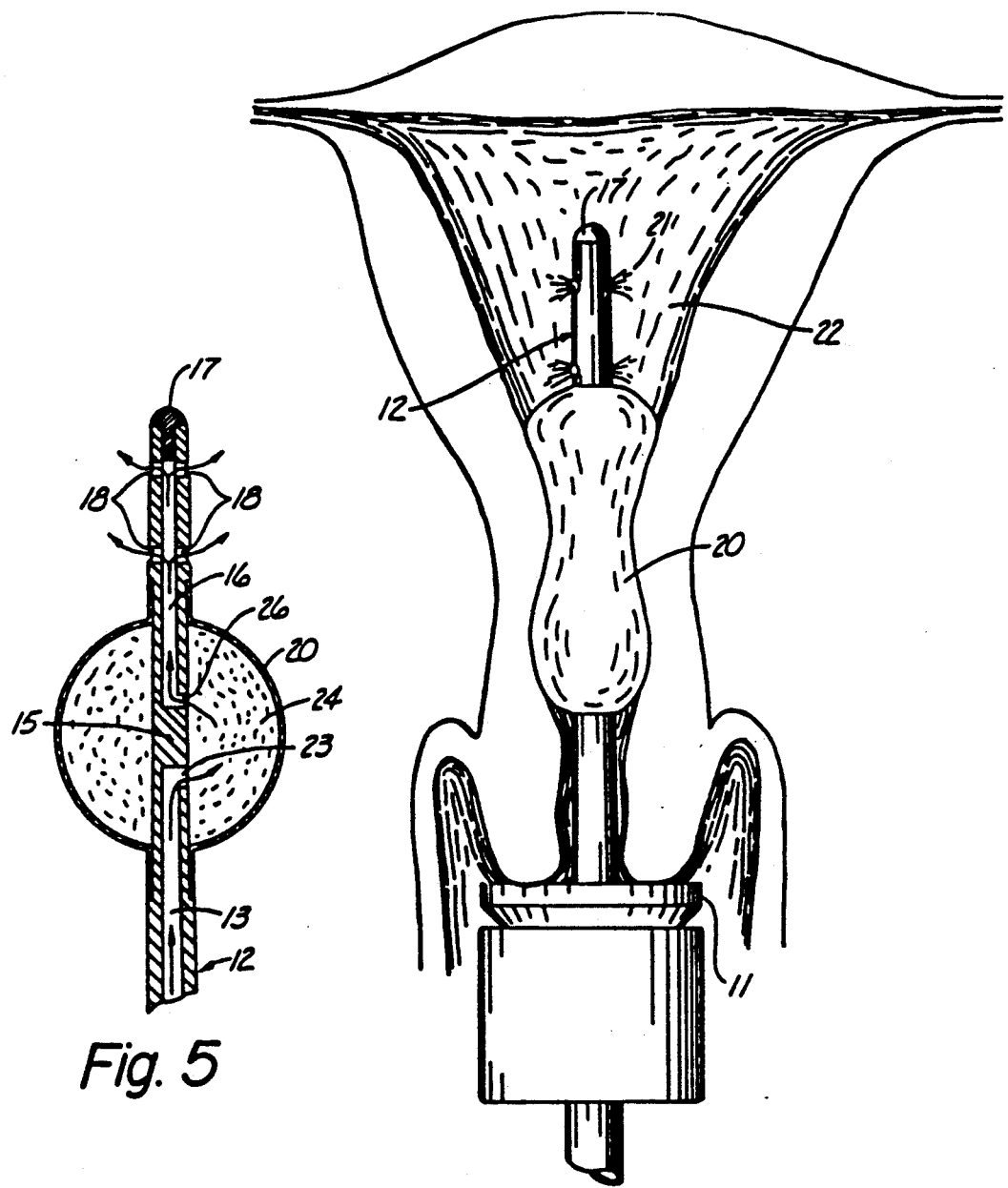
FIG. 5 is an enlarged cross sectional view similar to FIG. 3 but showing the apparatus when a high pressure fluid is connected to one end of the elongated member, illustrating how the balloon will inflate and the fluid will flow.
FIG. 6 is a somewhat cross sectional view of a uterine cavity showing the uterine injector in its operative position wherein the balloon tube is expanded to seal against the inner wall of the uterine cavity, while at the same time fluid is flowing into the uterine cavity.

Referring now to the drawings wherein like reference numerals designate identical or corresponding parts throughout the several views, FIG. 1 shows a uterine injector apparatus (10) constructed in accordance with the present invention. Attachment (11), which fits inside the head of a Valtchev uterine mobilizer, connects a source of liquid dye or liquid x-ray contrast medium to a source of such dye or x-ray medium under high pressure.

The attachment (11) is in fluid communication with an elongated member (12). A first fluid communication passageway (13) extends from the passageway (14) in the attachment (11) to a barrier (15). A second fluid communication passageway (16) extends from the barrier (15) to the other end of the elongated member (12). The extreme other end of the elongated member (12) has a plug (17) in the end thereof to force liquid through openings (18). The plug (17) also causes a smooth end on the elongated member (12) to prevent damage to the patient.

The passageway (13) has a sidewall opening (23) therein and the passageway (16) has an opening (26) therein. A tubular balloon-like member (20) is bonded in a groove to the elongated member (12) at each end thereof as can readily be seen in FIG. 5, but the center portion of the tube (20) is not bonded to the elongated member (12). The elongated tube (20) is of course sealed and is imperforate to the passage of fluids therethrough. It can be made of silicone rubber or the like.

In operation, after the cannula is inserted into the uterine cavity to the position shown in FIG. 6, a dye or x-ray contrast medium (21) is injected through the passageway (13). The fluid (21) enters the balloon cavity through the opening (23) and distends the balloon to the position shown in FIG. 6.

The distended balloon or tube (20) seals the exit from the uterine cavity (22). The fluid (21) then enters from the balloon cavity (24) (FIG. 5) through a very small opening (26), which is several times smaller than the cross sectional size of the opening (23), and then the flow goes into the passagEway (16) and out through sidewall openings (18), where it enters the uterine cavity and the fallopian tubes.

If there is a constant flow of fluid through the opening (23), the pressure inside the balloon (20) will be higher than in the uterine cavity (22). This is due to the resistance created by the smaller opening (26) on the fluid flowing from the balloon cavity (24) to the passageway (16). When the injection of fluid ceases, the pressure in the balloon drops and its sealing effect diminishes.

In its preferred embodiment, the opening (26) has a 0.1 mm diameter round opening and the opening (23) has a diameter of 2.0 mm in a round opening. A 20 ml syringe is used to inject the fluid into the passageway (13).

Figure 7:
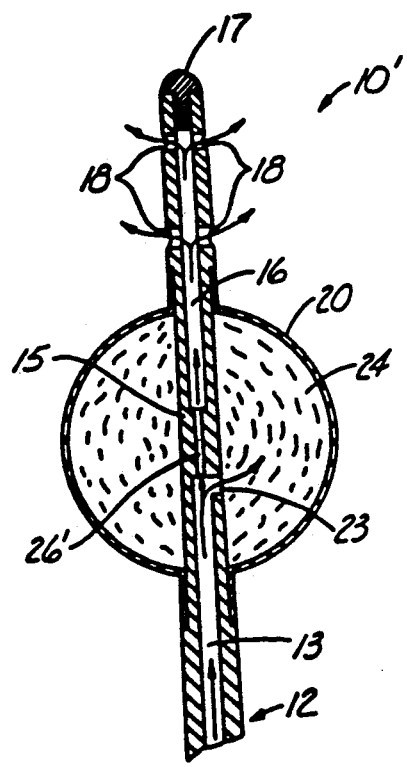
FIG. 7 is a cross sectional view like FIG. 5, but showing an alternate embodiment.

The FIG. 7 embodiment 10' operates just like embodiment 10 except that opening 26' communicates passageway 16 directly with passageway 13. The diameter of 26' is much smaller than opening 23 so that it forms a restriction so that the balloon 20 will inflate as flow goes through passageway 26'.

Accordingly, it will be appreciated that the preferred embodiment disclosed herein does indeed accomplish the aforementioned objects. Obviously, many modifications and variations of the present invention are possible in light of the above teachings. It is therefore to be understood that, within the scope of the appended claims, the invention may be practiced otherwise than as specifically described.

I claim:

1. Apparatus for the injection of dye or contrast medium into a uterine cavity comprising:

an elongated member having a first end, a second end and an intermediate portion between the first and second ends;

a liquid impervious expandable tube disposed around said elongated member and being sealed at each end thereof to the exterior of said elongated member, said tube extending over said intermediate portion of said elongated member;

first means for forming a first fluid communication passageway from said first end to said intermediate portion of said elongated member;

second means for forming a second fluid communication passageway from said intermediate portion to said second end of said elongated member;

said first end of said elongated member being adapted to receive a source of liquid dye or contrast medium under pressure;

a first opening in said elongated member, said first opening being in fluid communication with said first fluid communication passageway with the inside of said tube;

a second opening in said elongated member, said second opening being in fluid communication with said second fluid communication passageway and with the inside of said tube;

barrier means disposed on the interior or said elongated member to prevent direct fluid communication between said first and second fluid communication passageway;

discharge means in open fluid communication with said uterine cavity and disposed in said second end of said elongated member for permitting fluid in said second fluid communication passageway to exit therethrough; and said second opening being substantially smaller in said cross-sectional area than said first opening whereby the fluid pressure inside of said tube will be substantially higher than the pressure in said second fluid communication passageway whereby the fluid pressure within the tube will cause it to expand to seal against the inner wall of the uterine cavity while at the same time fluid will flow sequentially from the fiirst fluid communication passageway, through the first opening,, through the expanded tube, through the second opening, through the second fluid communication passageway and out the open discharge means into said uterine cavity.

2. The apparatus of claim 1 wherein said discharge means includes a plurality of holes in the second end of said elongated member.

3. The apparatus of claim 2 wherein a rounded plug is disposed in the second fluid communication passageway of said second end of said elongated member.

4. The apparatus of claim 3 wherein said elongated member is straight except for being curved on the second end thereof.

* * * * *